United States Patent [19]

Fujiwara et al.

[11] Patent Number: 5,209,569
[45] Date of Patent: May 11, 1993

[54] APPARATUS FOR MEASURING THERMAL DIMENSIONAL CHANGE OF CERAMICS OR THE LIKE

[75] Inventors: Teiichi Fujiwara; Toshisada Mimura, both of Okayama; Toshiaki Hisanari, Bizen, all of Japan

[73] Assignee: Shinagawa Refractories Co., Ltd., Japan

[21] Appl. No.: 834,267

[22] PCT Filed: Aug. 16, 1990

[86] PCT No.: PCT/JP90/01044
§ 371 Date: Feb. 14, 1992
§ 102(e) Date: Feb. 14, 1992

[87] PCT Pub. No.: WO91/02968
PCT Pub. Date: Mar. 7, 1991

[30] Foreign Application Priority Data
Aug. 21, 1989 [JP] Japan .................. 1-213027

[51] Int. Cl.$^5$ .................. G01N 25/16
[52] U.S. Cl. .................. 374/55; 374/130
[58] Field of Search .................. 374/55, 56, 6, 7, 130

[56] References Cited
U.S. PATENT DOCUMENTS
3,930,730 1/1976 Laurens et al. .................. 374/6 X
5,121,987 6/1992 Berg .................. 374/55

FOREIGN PATENT DOCUMENTS
61-172041 8/1986 Japan .
62-109315 5/1987 Japan .
1-272950 10/1989 Japan .

Primary Examiner—Daniel M. Yasich
Attorney, Agent, or Firm—Larson & Taylor

[57] ABSTRACT

A laser beam-transmitting section of a laser measuring instrument of dimensional change is arranged at one side of a specimen heating furnace, a laser beam-receiving section is arranged at the opposite side of the furnace, a slit fixture for shielding within-the-furnace radiation heat and light is provided inside a measuring window, a heat insulating material having a slit for shielding within-the-furnace radiation heat and light is provided inside said slit fixture, and a within-the-furnace radiation light shielding slit plate and a within-the-furnace radiation light reducing optical filter are disposed at the end faces of said respective laser beam-transmitting section and said laser beam-receiving section whereby measuring errors caused by the light and heat generated within the furnace are prevented (the interior of a specimen heating furnace core pipe can be replaced by various kinds of atmospheres as necessary, and it is possible to measure the dimensional change of small-size specimens of ceramics or the like). According to the present apparatus for measuring thermal dimensional change of ceramics or the like, measurement is possible with a resolution of not greater than 0.5 μm.

7 Claims, 4 Drawing Sheets

APPARATUS FOR MEASURING THERMAL DIMENSIONAL CHANGE OF CERAMICS OR THE LIKE

INDUSTRIAL FIELD OF THE INVENTION

This invention relates to an apparatus for the precise and automatic measuring of thermal dimensional change [such as thermal linear expansion coefficient (hereinafter referred to as thermal expansion coefficient) or creep deformation rate] mainly of ceramics and the like under high temperature by using a laser measuring instrument and in non-contact type.

PRIOR ART

The thermal expansion coefficient of fine ceramics, refractories, pottery and porcelain, glass or ceramics of composite materials thereof with metal, or a variety of metals is one of the most important properties, which guides the determination of expansion joint of the lining refractories of furnace used in the hot state. Conventionally there are known, as prior art, Japanese Patent Kokai No. 39,540/85 relating to "Apparatus for Measuring Thermal Expansion Coefficient", Japanese Patent Kokai No. 7,452/86 relating to "Apparatus for Measuring Thermal Dimensional Change of Ceramics or the Like", and Japanese Patent Kokai No. 172,041/86 relating to "Apparatus for Measuring Thermal Dimensional change of Ceramics or the like".

As an example of the known techniques Patent Kokai No. 39,540/85 which is concerned with an apparatus for measuring thermal expansion coefficient is illustrated in FIG. 6. This apparatus is to automatically measure the thermal dimensional change of a specimen by combining two pairs each of a dimensional change measuring apparatus consisting of cameras 22 combined with lens systems 21 each internally housing a solid scanning photo diode elements and consisting of camera control units 23, and of an illumination means 24. The dimensional change of a specimen 8 within a heating furnace 1 is measured in such a way that the specimen is illuminated by the illumination means 24 from the right angular direction to the axis of the specimen, and the dark portion for which light has been shielded by the specimen and the light portion for the light has reached directly are magnifyingly projected on the surface of the solid scanning photo diode elements by the telephoto lens 21 thereby relying on the ratio of the light portion to the dark portion. In such a case the outputs of the two camera control units 23 are added and the output is made by the digital output signal according to the dimensional change.

The output thus produced and the digital output signal of a digital thermometer 13 are input into a computer 15 through an interface 14 when a storage operation is effected, and the relation between the temperature and the thermal expansion coefficient is graphed by a digital plotter 16.

According to this method, however, the measuring range by one camera 22 is only about 3 mm in the case of 1 μm measuring resolution. Further, in case two cameras 22 are used in parallel to increase the measuring precision there is an 80 mm space between the two cameras, so that only specimens having a dimension not smaller than 80 mm can be measured.

These days, as fine ceramics and the like have been developed a measurement for small-size specimens is desired. To meet such requirement specimens having a dimension of not greater than 80 mm are measured either by fixing a prism 25 at the end of each camera 22 as shown in FIG. 7 or by positioning two cameras 22 oppositely as described in Japanese Patent Kokai No. 172,041/86 which relates to "Apparatus for Measuring Thermal Dimensional Change of Ceramics or the Like". However, the resolution of the solid scanning photo diode element camera 22 is limited to 1 μm, and since the expansion rate is small in the case of small-size specimens a resolution in the sub-micron order is required these days.

Further, the measuring range of one camera 22 unit using the solid scanning photo diode element is about 3 mm, so that there arises a problem that it is impossible to measure abnormally expanding specimens or greatly shrinking specimens.

DISCLOSURE OF THE INVENTION

The present invention relates to an apparatus for measuring thermal dimensional change of ceramics or the like characterized in that instead of using a solid scanning photo diode element as in the known techniques, a laser beam-transmitting section of a laser measuring instrument is arranged at one side of a specimen heating furnace, a laser beam-receiving section is arranged at the opposite side, a slit fixture for shielding within-the-furnace radiation heat and light is provided inside a measuring window, a heat-insulating material having a slit for shielding within-the-furnace radiation heat and light is provided inside said fixture, and a within-the-furnace radiation light shielding slit plate and a within-the-furnace radiation light reducing optical filter are disposed at the end faces of said respective laser beam-transmitting section and said laser beam-receiving section whereby measuring errors caused by the light and heat within the furnace are prevented (the interior of the specimen heating furnace core pipe can be replaced by various kinds of atmospheres as necessary, and it is possible to measure the dimensional change of small-size specimens of ceramics or the like) and a measurement is possible with a resolution or not greater than 0.5 μm.

BRIEF DESCRIPTION OF THE DRAWINGS

FIG. 4b is a sectional view taken along the line A—A of FIG. 4a;

BEST MODE FOR CARRYING OUT THE INVENTION

An embodiment of applying the apparatus for measuring thermal dimensional change of ceramics or the like according to the present invention to an apparatus for measuring thermal expansion coefficient is described in detail with reference to FIG. 1 of the drawings.

Figure 1:
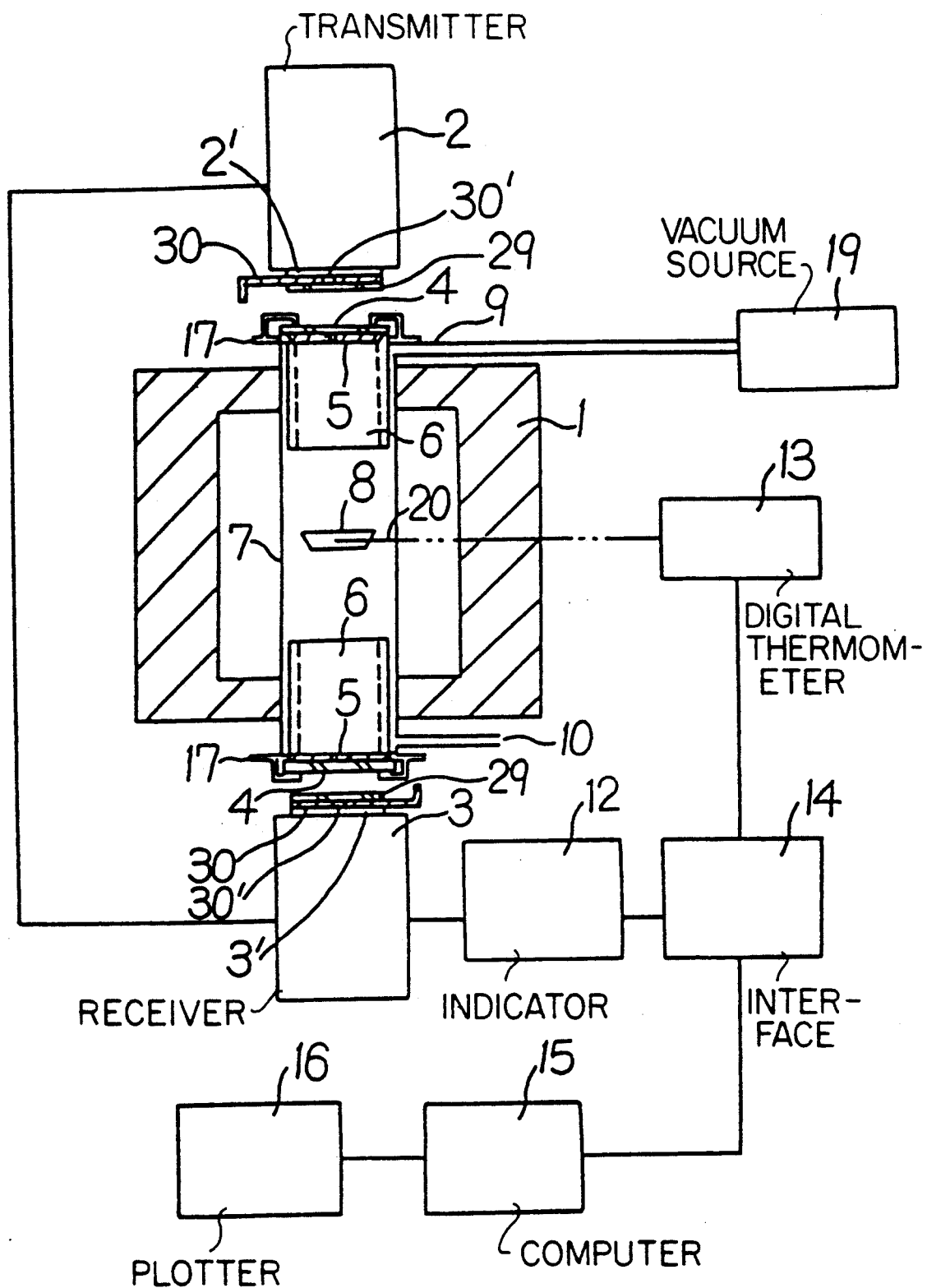
FIG. 1 is a schematic view of one embodiment of the present apparatus.
Figure 2A:
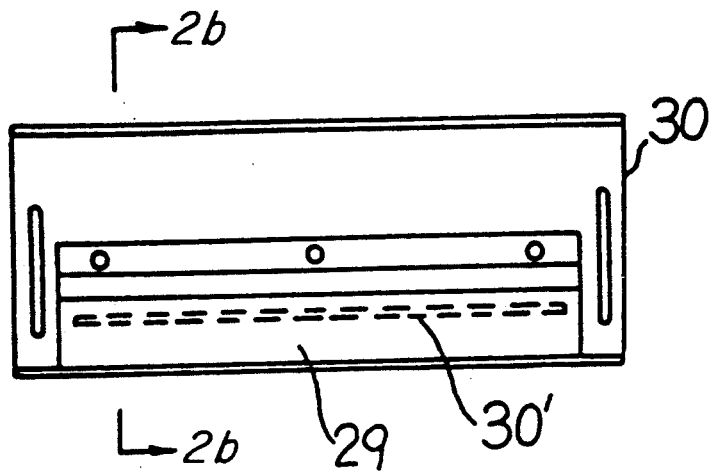
FIG. 2(a) is a front view of an assembly body of the within-the-furnace radiation light reducing filter and the within-the-furnace radiation light shielding slit plate which are mounted to the laser beam-transmitting port and the laser light-receiving port respectively.
Figure 2B:
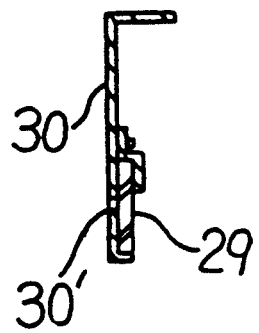
FIG. 2(b) is a sectional view taken along the line C—C of FIG. 2(a)

As a method of measuring the dimensional change of a small-size specimen precisely and with a resolution in the sub-micron order, the measuring apparatus of FIG. 1 is constructed in such a way that a measuring window (of quartz glass) 4 is provided at each of the two ends of a furnace core pipe 7 supporting a specimen 8 within a heating furnace 1 so that the interior of said pipe 7 can be made gas-tight, and an exhaust port 9 connected to a vacuum or suction source 19 and a gas guiding inlet 10 are provided at the respective ends of said pipe 7 whereby the thermal dimensional change of the specimen 8 can be measured at various atmospheres. By providing the measuring windows 4, a heat insulating material 6 having a within-the-furnace radiation heat shielding slit inside said windows, and within-the-furnace radiation light shielding slit fixtures 5 the measuring window 4 glass is prevented from deformation and errors causing due to the heat within the furnace, and by arranging a within-the-furnace radiation light shielding slit plate 30 and a within-the-furnace radiation light reducing filter 29 as shown in FIGS. 2a (front view) and 2b (sectional view) at the respective end faces of the beam-transmitting port 2' of a laser beam-transmitting section 2 and the beam-receiving inlet 3' of a laser beam-receiving section 3 the specimen 8 is prevented from causing measuring errors for dimensional change when the light within-the-furnace is emitted to the laser beam-transmitting section 2 and the laser beam-receiving section 3 in measuring the specimen at high temperature.

Said within-the-furnace radiation light shielding slit plate 30 is provided with a within-the-furnace radiation light reducing slit 30', the width of the slit is as referred to below, and as the optical filter 29 a light reducing filter usually used will suffice, but preferably it is a narrow band pass filter through which only laser beams can pass.

Figure 3:
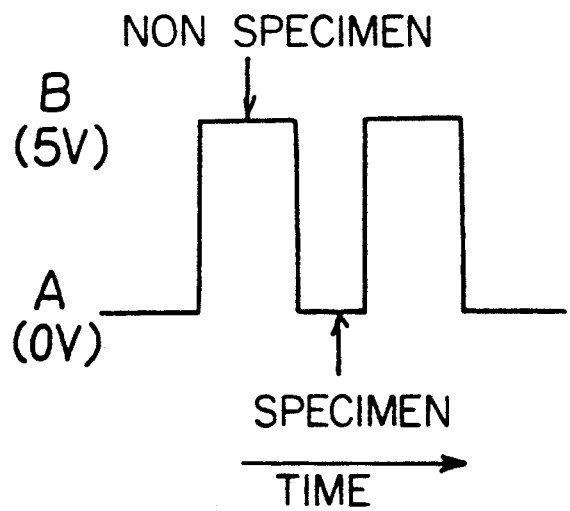
FIG. 3 shows a voltage signal of the laser beam-receiving section.

As shown in FIG. 1, referring to the dimensional change of the specimen 8, if laser beams scanned with a width wider than the length of the specimen 8 are emitted horizontally and at a certain speed from the laser beam-transmitting section 2 of the laser dimensional change measuring instrument while arranging said section 2 at one side of the two measuring windows (of quartz glass) 4 each having parallel and smooth surfaces and being mounted at the opening portions of both the ends of the furnace core pipe 7 and providing the laser beam-receiving section 3 at the opposite measuring window 4, a voltage signal does not generate as in A of FIG. 3 at the laser beam-receiving section 3 when the laser beams are intercepted by the specimen 8, but it generates as in B of FIG. 3 when the laser beams slip away from the specimen. In measuring the dimensional change of the specimen 8, the period of time during which the laser beams are intercepted by the specimen i.e. the time when the voltage signal of the laser beam-receiving section 3 is zero is measured electrically and precisely, the measuring result is digitally indicated by an indicator 12, and a digital output signal is output. This output signal and the digital output signal of a digital thermometer 13 for measuring the specimen temperature are input into a personal computer 15 through an interface 14 thereby carrying out a storage operation to allow a digital plotter 16 to record in a curve the relationship between the temperature and the thermal expansion coefficient.

When in the present apparatus the measuring windows (of quartz glass) 4 mounted to the opening portions at both the ends of the furnace core pipe 7 are deformed due to the high temperature within the furnace, the window glass causes a lens effect when the length of the specimen 8 is measured different from the practical size and great errors occur, so that a high precision measurement is impossible. At high temperatures not less than 1,000° C. the radiation light emitted from the interior of the furnace core pipe 7 becomes strong, and unnecessary light enters he laser beam-receiving section 3 and the laser beam-transmitting section 2, making the precise measuring of the dimension of the specimen impossible. To eliminate such a disadvantage, the apparatus of the present invention is constructed such that there is used a measuring window glass made of quartz glass with less thermal expansion coefficient and having less lens effect and parallel surfaces, there are provided inside each of the measuring windows 4 the slit fixture 5 having a within-the-furnace radiation heat and light shielding slit 11 whose width is 1.2 to 7 times that of a laser beam, and the heat insulating material 6 so as not to cause a deformation to the measuring windows 4 owing to the heat within the furnace, and at the beam-transmitting port 2' of said laser beam-transmitting section 2 and the beam-receiving port 3' of said laser beam-receiving section 3 there are arranged respectively the within-the-furnace radiation light shielding slit plate 30 equipped with a slit 30' whose width is 1.0 to 1.5 times that of the laser beam, and the within-the-furnace radiation light reducing optical filter 29 which reduces the intensity of the within-the-furnace radiation to $\frac{1}{2}$ to 1/10 whereby the radiation heat and light emitted from the interior of the furnace hardly enter into the laser beam-transmitting section 2 and the laser beam-receiving section 3.

If the width of the slit fixture 5 and the width of the radiation heat and light shielding slit 11 of said heat insulating material 6 are not broader than 1.2 times the width of the laser beam, the center of the laser beam and that of the slit get out of position in case the heating furnace 1 and the furnace core pipe 7 expand due to the heat, when the laser beam is intercepted by the slit fixture 5 and the heat insulating material 6 thereby causing sometimes an impossible measuring of the thermal dimensional change of the specimen 8. If the width of the slit is broader than seven times that of a laser beam to the contrary, the radiation heat is transmitted to the measuring window glass 4 to allow the glass to be deformed by the heat thereby causing measuring errors, and unnecessary light emitted from within-the-furnace enters in large quantity into the laser beam-transmitting section 2 and the laser beam-receiving section 3 thereby to cause a great error in measuring the thermal dimensional change of the specimen 8.

Further, if the width of the slit 30' of said within-the-furnace radiation light shielding slit plate 30 being provided at each of the beam-transmitting port 2' of said laser beam-transmitting section 2 and the beam-receiving port 3' of said laser beam-receiving section 3 is less than 1.0 time the width of a laser beam, the laser beam is weakened to cause impossible measuring of the dimensional change of a specimen. On the other hand, if the width of the slit 30' of said slit plate 30 is more than 1.5 times that of the laser beam the effect of shielding the within-the-furnace radiation light is reduced.

The optical filter 29 disposed at each of said beam-transmitting port 2' and said beam-receiving port 3' may be either such one which reduces, in the same proportion, the passing quantities of the within-the-furnace radiation light and the laser beam or such one having properties where only the laser beam is selectively passed through and the passing quantity of the within-the-furnace radiation light is reduced.

Figure 4B:
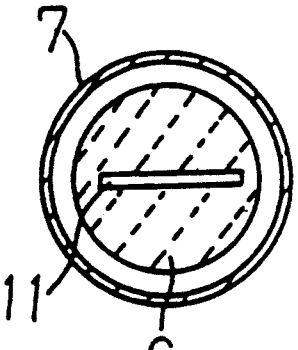
Figure 4A:
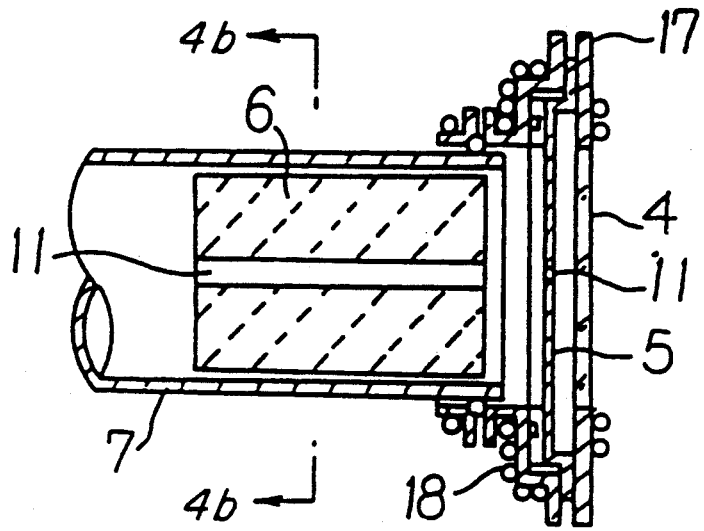
FIG. 4a is a vertical sectional view showing one embodiment of the heat insulating material for shielding the radiation light and heat and the measuring window fixture.

The metallic fixture 17 of a measuring window 4 is constructed in such a way that as shown in FIG. 4 it is made water-cooling system being provided with water-cooling pipes 18, the metallic slit fixture 5 of shielding the radiation light for the measuring window 4 is made of a highly heat-conductive metallic material, and said slit fixture 5 is arranged in the furnace side inside the measuring window (of quartz glass) 4 in close contact with a metallic fixture 17 whereby the cooling effect is enhanced and the rise of temperature of the window 4 is completely prevented.

Thus, the temperature of the measuring window 4 does not rise and the window is not deformed so that the unnecessary light within the furnace is emitted minimum into the laser beam-transmitting section 2 and the laser beam-receiving section 3 to allow the thermal dimensional change of a specimen to be measured precisely.

EXAMPLE

Figure 5:
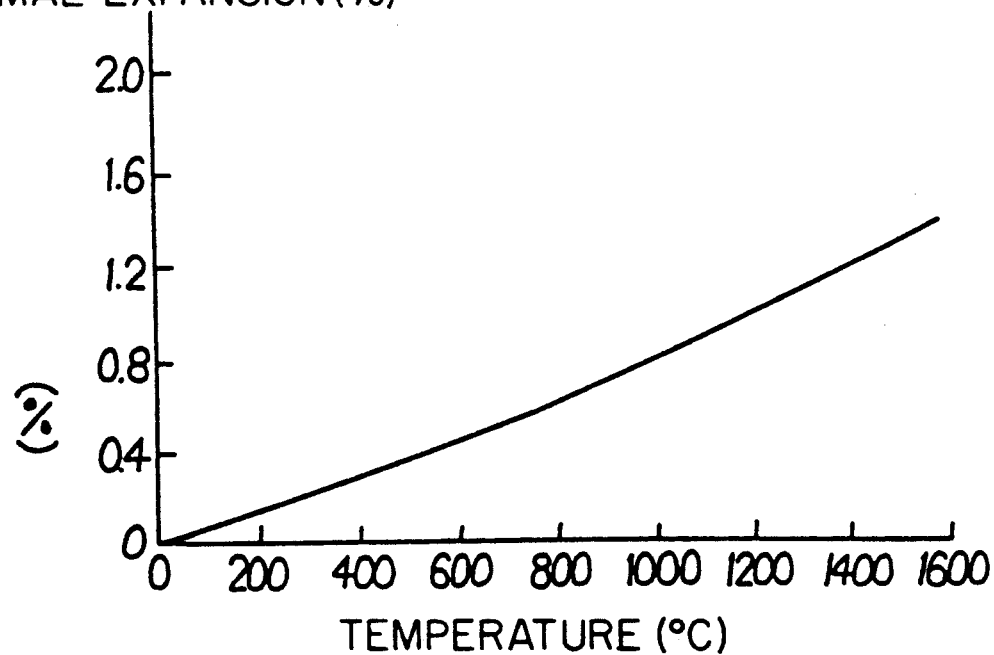
FIG. 5 shows an example of the measuring result obtained according to the present apparatus.
Figure 6:
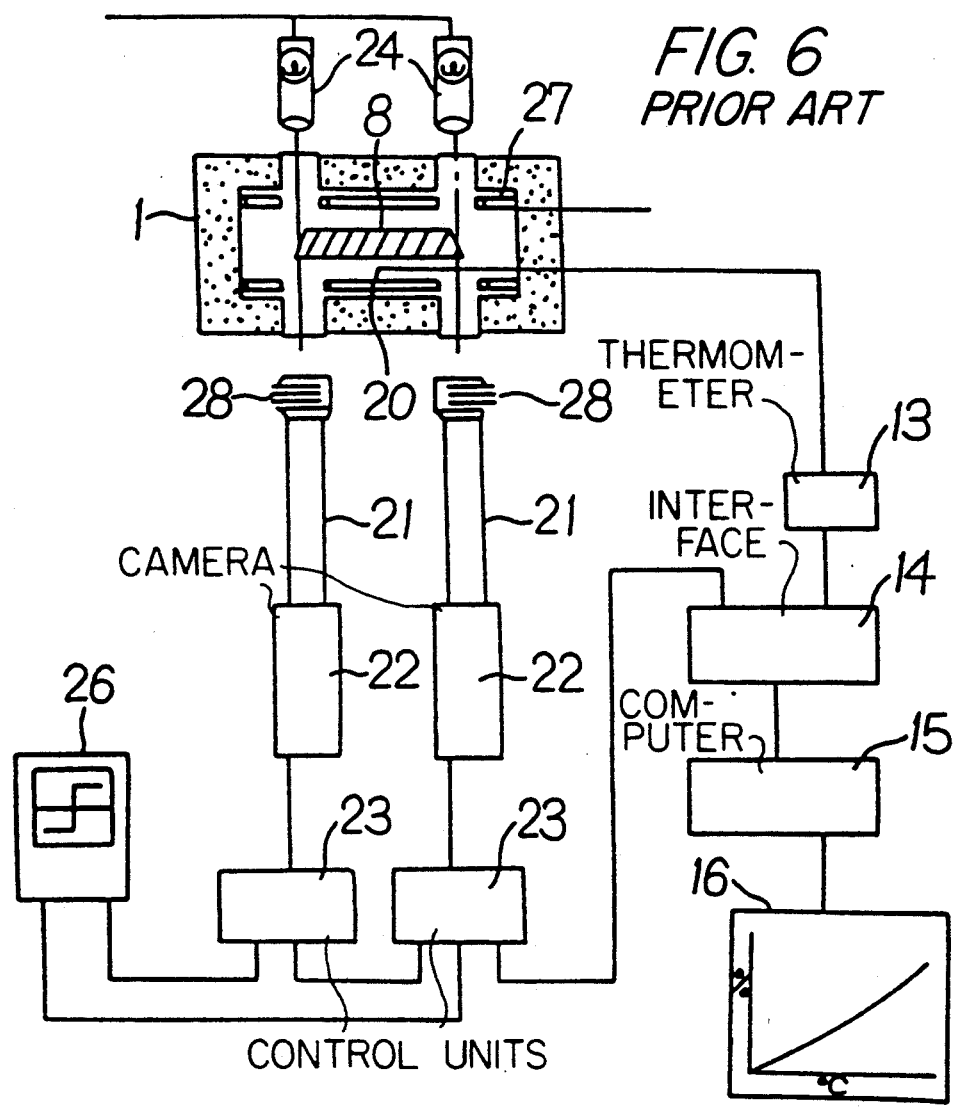
FIG. 6 is a schematic view of an example of a known thermal expansion measuring apparatus using a fixed scanning beam-receiving component.
Figure 7:
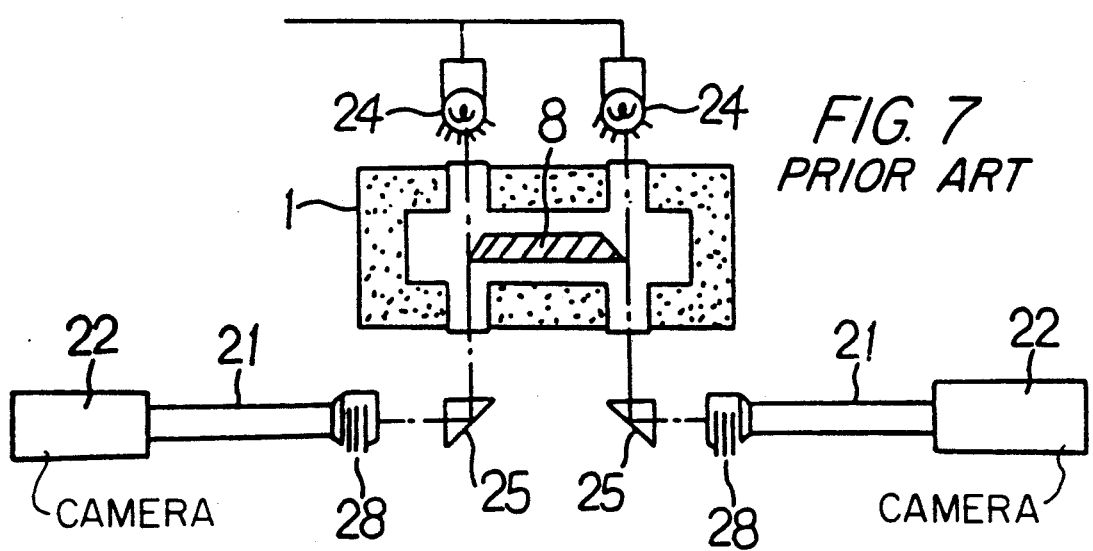
FIG. 7 is a schematic view of an example of a known thermal expansion measuring apparatus using a prism.

The measuring windows 4 of the present apparatus shown in FIG. 1 were provided with quartz glass of 3 mm thick and having parallel surfaces. An aluminous specimen of 10 mm wide × 10 mm high × 40 mm long was set in a furnace core pipe 7, and an inert gas was flown thereinto at the rate of 150 ml per minute. As a laser measuring instrument of dimensional change of the specimen was used the one the measuring range of which is 0.5 to 55 mm and in which the distance between the beam-transmitting section 2 and the beam-receiving section 3 is 700 mm. Inside the measuring windows 4 at both the ends of the furnace core pipe 7 there were fixed the radiation light and heat shielding, heat insulating material 6 and the radiation light shielding slit fixtures 5, each of said material and fixtures having a slit of 2 mm wide × 60 mm long. Then, in the beam-transmitting port 2' of said laser beam-transmitting section 2 and the beam-receiving port 3' of said laser beam-receiving section 3 there were respectively mounted the slit plates 30 and the filters 29 through which a laser beam selectively passes and which reduces the within-the-furnace radiation light, each of the slit plate 30 and the filter 29 having a slit 30' of 1.2 mm wide × 55 mm long. The temperature-rising rate was set to 4° C., the data between room temperature and 1,800° C. were read every 5° C., and the data were subject to a storage operation. The effect in which the digital plotter 16 read the relationship between the temperature and the thermal expansion coefficient is shown in FIG. 5.

INDUSTRIAL APPLICATION OF THE INVENTION

The present invention is useful particularly for the precise and automatic measuring of thermal dimensional change [such as thermal expansion coefficient or creep deformation rate] mainly of ceramics and the like under high temperature by the use of a laser measuring instrument and in a non-contact type.

We claim:

1. An apparatus for measuring thermal dimensional change of ceramics and the like, comprising a furnace for heating a specimen to be tested, a furnace core pipe passing through said furnace for receiving the specimen to be tested and including end faces at opposite ends thereof and measuring windows provided at said end faces, a laser dimensional change measuring instrument for measuring thermal dimensional change including a laser-beam transmitting section arranged at one end of said furnace core pipe and a laser beam-receiving section arranged outside the other end of said core pipe, a within-the-furnace radiation heat and light shielding slit metal fixture provided inside each of said measuring windows, a heat insulating material disposed inside said slit metal fixture and including a within-the-furnace radiation heat and light shielding slit, and a within-the-furnace radiation heat shielding slit plate and an optical filter arranged respectively at the end faces of said laser beam-transmitting section and said laser beam-receiving section.

2. An apparatus according to claim 1 wherein said laser dimensional change measuring instrument comprises a laser beam scanning instrument.

3. An apparatus according to claim 1 wherein said core pipe is made gas-tight and is provided with an atmospheric gas feed-exhaust pipe for enabling various kinds of atmospheres to be produced within said core pipe.

4. An apparatus according to claim 1 wherein the width of said within-the-furnace radiation heat and light shielding slit provided at each of said heat insulating material and said measuring window glass portion is in the range of 1.2 to 7 times the width of a laser beam.

5. An apparatus according to claim 1 wherein the width of the within-the-furnace radiation light shielding slit arranged at each of said laser beam-transmitting section and said laser beam-receiving section is 1.0 to 1.5 times the width of the laser beam.

6. An apparatus according to claim 1 wherein said measuring window glass is provided with a cooling structure in order to prevent the glass from deforming and to avoid measuring errors.

7. An apparatus according to claim 1 wherein said measuring window glass is made of quartz glass having a high heat-resistant property and a small thermal expansion coefficient as well as parallel surfaces.

* * * * *